United States Patent [19]

Maes

[11] Patent Number: 5,183,751
[45] Date of Patent: Feb. 2, 1993

[54] STABILIZATION OF PEROXIDASE SOLUTIONS BY PARA-AMINO-SALICYCLIC ACID

[76] Inventor: Roland F. Maes, Bildhauerhof 34, Rosheim 67190 Mutzig, France

[21] Appl. No.: 693,537

[22] Filed: Apr. 30, 1991

Related U.S. Application Data

[63] Continuation-in-part of Ser. No. 326,790, Mar. 21, 1989, abandoned.

[30] Foreign Application Priority Data

Apr. 20, 1988 [FR] France ................................. 85 05243

[51] Int. Cl.$^5$ ................................................ C12N 9/96
[52] U.S. Cl. ........................................ 435/188; 435/28; 435/192
[58] Field of Search ............................ 435/188, 192, 28

[56] References Cited

U.S. PATENT DOCUMENTS

| | | | |
|---|---|---|---|
| 3,627,698 | 12/1971 | Rey et al. ............................ | 252/408 |
| 4,252,896 | 2/1981 | Shaffar ................................... | 435/7 |
| 4,900,671 | 2/1990 | Pokora et al. ....................... | 435/156 |

Primary Examiner—Douglas W. Robinson
Assistant Examiner—S. Saucier
Attorney, Agent, or Firm—William J. Daniel

[57] ABSTRACT

Para-amino-salicylic acid (PASA) or a water-soluble salt thereof, e.g. of an alkali metal, alkaline earth metal, ammonia or an amine is used for the stabilization of the enzymatic activity of peroxidase in aqueous medium. The stabilizing agent may be in the form of an aqueous solution compatible with peroxidase medium in which PASA or its salt is dissolved in a quantity efficacious for stabilization, preferentially comprised between about 8 µg/ml and about 2000 µg/ml of the solution based on PASA. With such stabilizing agent, one can efficaciously stabilize solutions of peroxidase, whether free or conjugated to immunological carrier reagents, and prepare these reagents in advance in a diluted form ready for use.

13 Claims, No Drawings

STABILIZATION OF PEROXIDASE SOLUTIONS BY PARA-AMINO-SALICYCLIC ACID

CROSS-REFERENCE TO RELATED APPLICATION:

This application is a continuation-in-part of my application Ser. No. 07/326,790, filed Mar. 21, 1989, now abandoned.

FIELD OF THE INVENTION

The present invention relates to the use of para-amino-salicylic acid (PASA) for the stabilization of the enzymatic activity of peroxidase solutions, the stabilizing agent per se and peroxidase solutions stabilized thereby.

BACKGROUND OF THE INVENTION

Horseradish peroxidase is a frequently used enzyme in diagnostic tests based on enzyme-immunological reactions. Among these, one may mention pregnancy tests and tests for the detection of antiviral antibodies, such as hepatitis, human immuno-deficiency virus (HIV) and rubella.

Peroxidase, whether coupled or not to immunological carrier reagents, is unstable in diluted form in aqueous solution. This compels the test reagent manufacturer to supply the enzyme as a dry powder or in a concentrated form in a aqueous medium containing stabilizing agents such as bovine albumin or serum, whose concentrations may be as high as 20% of the total reagent volume. The user is thus required to carry out a dilution of the reagent at the moment of use, which may result in error and additional costs and is in any case inconvenience.

It is therefore advantageous to find stabilizing substances that allow the production of peroxidase and peroxidase-coupled reagents in stable diluted form in an aqueous medium, ready to use, with the optional additional requirement of being effective at a pH near neutrality.

Various investigations aimed at identifying stabilizing agents for peroxidase have been made, resulting in the following patents:

DE 3509238, corresponding to EPA 0 196 518 from Boehringer Mannheim

DE 3511 327, corresponding to EPA 0 197 447 also from Boehringer, which discloses the incorporation of phenol or aminopyrine at a concentration equal or superior to 0.0005%

CH 4944184, corresponding to EPA 0 070 992 from Hoffman-La Roche, claiming 4-amino-antipyrine; and USP 4,252,896 from Abbott disclosing the use of anilino-8-naphtalene-sulfonic acid.

None of these substances achieves satisfactory stabilization of peroxidase solutions.

OBJECT AND SUMMARY OF THE INVENTION

The aim of this invention is to solve the above technical problem by the provision of a new stabilizing agent of the enzymatic activity of peroxidase solutions, be it at 4° C. or at room temperature, which is effective for at least 10 days.

These technical problems have now solved for the first time by the present invention. It has indeed been found that para-amino-salicylic acid (PASA) either in free acid or salt form is endowed with remarkable stabilizing properties for the enzymatic activity of peroxidase in aqueous media, whether at low temperatures or at 37° C. for a period of at least 10 days.

This is quite surprising inasmuch as the meta-isomer 5-amino-salicylic acid, is a substrate of enzymatic reaction for peroxidase, making it unexpected to find among other derivatives of salicylic acid a compound able to stabilize the enzymatic activity of peroxidase.

GENERAL DESCRIPTION OF THE INVENTION

The invention thus concerns the use of para-amino-salicylic acid as a stabilizing agent of the enzymatic activity of peroxidase in aqueous media, whether free or coupled to an immunological carrier reagent.

A second aspect of the invention concerns the stabilizing agent itself, containing the PASA. An advantageous characteristic is to set the concentration of PASA between about 8 $\mu$g/ml and about 2000 $\mu$g/ml of the solution.

This stabilizing agent contains advantageously para-amino-salicylic acid solubilized in a buffer constituted of Tris brought to a pH comprised between about 7 and 8 with an acid chosen preferably among acetic acid, succinic acid, boric acid and diethylbarbituric acid.

This stabilizing agent may in addition contain at least 2% serum.

The present invention concerns finally an aqueous medium containing stabilized peroxidase, characterized in that it contains an adequate quantity of para-amino-salicylic acid or a salt thereof for the stabilization. Preferably, this efficacious quantity of PASA is comprised between about 8 $\mu$g/ml and about 2000 $\mu$g/ml of the total medium or a corresponding amount of the salt thereof.

This stabilized peroxidase-containing medium is preferentially a Tris buffer. Desirably, this medium contains also at least 2% serum. According to another mode of realization, the stabilized peroxidase-containing medium contains at least 0.01% in weight of $CaCl_2$ and at least 0.01% in weight of $MgCl_2 \cdot 6H_2O$.

Preferably, this stabilized medium is in ready for use condition, that is, without dilution or mixing with a concentration of peroxidase equal to less than 50 $\mu$g/ml of the total medium.

Finally, the invention concerns also the process of preparation of the stabilizing agent and of the stabilized peroxidase-containing medium that is apparent to the man of the art from what has been said as well as from the description that follows.

Other purposes, characteristics and advantages will appear at the light of the description that follows, and from the following examples that should not be in any way construed to limit the scope of this invention.

The enzyme peroxidase derived from horseradish roots is effective for catalyzing the oxidation of a number of organic compounds by hydrogen peroxide. This reaction can be employed to form colored end products and is utilized in a number of different analytical determinations such as, in addition to those identified before, the determination of glucose and galactose in biological fluids. Peroxidase is commercially available in several different forms, namely as an essentially salt-free powder, either affinity purified or not, as a crystalline suspension in 3.2M ammonium sulphate solution adjusted with potassium phosphate buffer to a pH of 6.0, or as an insoluble enzyme attached to agarose beads suspended in 2.0M ammonium sulphate with a ph of 7.0. One supplier is Calzyme Laboratories of San Luis Obisbo, Calif. or University of Birmingham Research Park, Birmingham England.

Peroxidase is soluble in distilled water or in dilute buffer solutions according to descriptive material from this supplier. In U.S. Pat. No. 4,378,429, peroxidase is described as being dissolved in an aqueous solution of potassium di-hydrogen phosphate adjusted with sodium hydroxide to a pH within the range of about 4 to about 9 to form as part of a colorimetric system in combination with 4-amino-antipyrine and phenol in the context of a method for determining total cholesterol in human serum utilizing cholesterol oxidase.

It is preferred that any buffer solution for dissolving the peroxidase be slightly alkaline in nature, say from pH 7.0 to about 8.0 although a somewhat higher pH is possible. A most preferred buffer solution is an aqueous solution of TRIS, i.e. trimethylol amino-methane which is readily available and well known in solution form as a pharmaceutical buffer recognized, according to Merck's Index, as useful as a pH 7-9 buffer. An alkaline buffering solution, such as TRIS, in addition to dissolving the peroxidase, aids in solubilizing the PASA, as will now be described.

PASA is conventionally employed for the treatment of tuberculosis and is sold for that purpose under a number of trade names according to Merck's Index. In its free acid form, PASA is only slightly soluble in water, one gram dissolving in about 500 ml water. In principle, such a solution could serve the purposes of the present invention since it contains PASA in a concentration within the limits effective for this invention. However, free PASA is known to be relatively unstable in aqueous solution, especially at higher temperatures at about above 40° C. On the other hand, PASA is recognized as being soluble in dilute nitric acid or advantageously for present purposes, in dilute sodium hydroxide, and such solutions are recognized at having a reduced tendency to undergo decomposition. Thus, the sodium salt of PASA is water-soluble to the extent of one gram in 2 ml water while the potassium salt is freely soluble with a pH at 1% concentration of about 7. The calcium salt is soluble to the extent of about 1 gram in 7 ml water and other alkaline earth metal salts have more or less comparable solubility. Similarly, the amine salts of PASA are sufficiently soluble for present purposes and TRIS, being an amine, is one useful example of amines suitable for solubilizing PASA as an amine salt. Other simple amines could be substituted for TRIS if desired. Ammonia will also produce a soluble PASA salt that could be effectively employed in the practice of this invention.

Since these PASA salts have considerably greater water-solubility than the free acid and tend to be more stable, they are usually more convenient to use, either directly or as formed in situ by addition of the free acid to an alkaline buffered solution of peroxidase, and hence are preferred in this invention.

As comparative data presented in the following examples establish, the stabilizing effect sought in the present invention is effectively provided by PASA when incorporated in dissolved form into the aqueous solution of the peroxidase. An effective stabilizing concentration based on PASA is from about 8 $\mu$g/ml solution to about 2000 $\mu$g/ml although the upper limit of this range is not strictly limiting but could be exceeded. Thus, in the following Example 4, PASA is employed with good stabilizing effectiveness at the concentration of 2500 $\mu$g/ml. The above specified range of concentration for PASA is determined based on the free acid form and if any of the various salt forms mentioned above is employed directly, the concentration range therefor would vary somewhat according to stoichiometrical equivalents. It need hardly be stated that the selected salt form of PBS would need to be innocuous for the particular purpose contemplated for the stabilized peroxidase solution and should thus be free from any deleterious consequences for that use.

An mentioned, peroxidase conjugated or bound in insoluble form to immunological carrier reagents, such as agarose beads, also exhibits instability when separated in aqueous media. PASA or its water-soluble salts are equally effective in stabilizing these complexes at concentrations as specified above.

EXAMPLE 1

4-amino-salicylic acid, also called para-amino-salicylic acid (PASA), sulfo-salicylic acid and 5-nitro-salicylic acid were each solubilized at a concentration of 2000 $\mu$g/ml in a solution 0.02M. Tris. The pH was adjusted in one Example to pH 8 with 0.025M. acetic acid and in another to pH 7 with 0.025M. succinic acid, except for sulfo-salicylic acid, which is acid.

Horseradish peroxidase was PODase added to these media and the solutions were kept at 4° C. and at 37° C. over 11 days. The residual enzymatic activity was measured by the introduction of 5 ul of each solution into 100 ul of a substrate of enzymatic reaction consisting in 0.4 mg ortho-phenylene diamine (OPD) solubilized in 1 ml of a citric acid-phosphate diamine at pH 5.3 containing 0.02% $H_2O_2$. After 10 minutes of incubation, the yellow colored reaction was stopped by the addition of 100 ul of 4 N $H_2SO_4$ and the intensity of the coloration was measured at 492 nm. The results of these experiments are summarized in Table 1.

TABLE 1

|                  | control | | acetic ac. | | succinic acid | |
| --- | --- | --- | --- | --- | --- | --- |
|                  | 37°  | 4°   | 37°  | 4°   | 37°  | 4°   |
| PODase control.  | 1.29 | 2.17 | 0.54 | 2.16 | 0.10 | 0.77 |
| PASA (invention) | 1.66 | 2.42 | 1.75 | 2.05 | 1.19 | 1.88 |
| Sulfo-salicyl.   | 0.13 | 2.20 | 0.83 | 2.22 | 0.15 | 1.50 |
| Nitro-salicyl.   | 0.24 | 1.88 | 0.73 | 2.02 | 0.15 | 1.20 |

The superiority of PASA is evident at 4° C. and particularly at 37° C. and also when the pH of the solution is brought down to 8 or 7. On the contrary, sulfo-salicylic and nitro-salicylic acid show little or no significant stabilizing activity versus the control.

EXAMPLE 2

The optimal concentration of PASA was then determined. Peroxidase was dissolved in a buffer Tris-barbituric acid in the presence of various concentrations of PASA and held over 9 days at 4° C. and 37° C. The residual enzymatic activity was analyzed as per Example 1 and the results reported in Table 2.

TABLE 2

| PASA concentration | 37° C. | 4° C. |
| --- | --- | --- |
| 0 $\mu$g/ml | 0.40 | 2.0 |
| 8 | 0.79 | 1.97 |
| 40 | 1.11 | 2.0 |
| 200 | 1.52 | 2.0 |
| 1000 | 1.65 | 2.0 |

The PASA concentration is in μg/ml and the O.D. were read 292 nm. It is clear from the results here shown that the stabilizing effect of PASA takes place at concentrations as low as 8 μg/ml but is optimal at 200 μg/ml or higher.

EXAMPLE 3

Peroxidase was dissolved at a concentration of 0.6% in Tris, buffer solution, to which was added 0.04% concentration of boric acid and 0.05% (500 μg/ml) if PASA. This solution was supplemented with 2% turkey serum and this solution as well as the starting peroxidase Tris solution were incubated at 4° C. and 37° C. over 7 days, after which an analysis was made of the residual enzymatic activity. Results are given in Table 3.

TABLE 3

| Control | | Serum | |
|---|---|---|---|
| 37° C. | 4° C. | 37° C. | 4° C. |
| 0.4 | 1.38 | 1.40 | 1.59 |

One sees that the enzymatic activity of the peroxidase solution is well maintained at 37° C. in the presence of serum.

EXAMPLE 4

Anilino-8-naphthalene-1-sulfonic acid (ANSA), phenol, aminopyrine and 4-amino-antipyrine were applied according to the recommendations given in the patents identified above and compared to the enzymatic activity of PODase solubilized in a medium that was 0.9% in NaCl, buffered at pH 8.0 with Tris-acetic acid 0.05M., containing 5% serum, 0.25% PASA and 0.1% CaCl$_2$—MgCl$_2$·6 H$_2$O.

The solution formed a precipitate that was discarded through filtration, before the addition of the enzyme. The solutions were placed at 37° C. and 4° C. over 7 days and analyzed according to Example 1. Results are given in Table 4.

TABLE 4

| | Invention | Prior art | | | |
|---|---|---|---|---|---|
| | PASA | Aminopyrine | Phenol | Antipyrine | ANSA. |
| 37° C. | 1.78 | 0.4 | 0.0 | 0.55 | 1.1 |
| 4° C. | 1.73 | 1.5 | 1.2 | 1.40 | 1.5 |

PASA is superior to the other substances tested. This stability of the enzyme is also observed at 4° C. and remained fully undiminished at 37° C., contrary to what is observed with the substances advocated in the prior art.

I claim:

1. A method for stabilizing the enzymatic activity of horseradish peroxidase contained in an aqueous medium which comprises incorporating in said medium a stabilizing amount of para-amino-salicylic acid (PASA) or water-soluble salt thereof.

2. The method of claim 1, wherein said medium contains not more than 50 μg/ml of said peroxidase.

3. The method of claim 1, wherein the amount of said para-amine-salicylic acid or said salt in said medium corresponds to the range of about 8–2000 μg of PASA per ml of medium.

4. The method of claim 1, wherein said water-soluble salt is of an alkali or alkaline earth metal, ammonia or an amine.

5. The method of claim 1 wherein said peroxidase is bound to immunological carrier particles suspended in said aqueous medium.

6. A stabilized aqueous solution of horseradish peroxidase consisting essentially of horseradish peroxidase and an effective stabilizing amount of para-amino-salicylic acid in aqueous solution.

7. The stabilized solution of peroxidase according to claim 7, wherein the amount of said para-amine-salicylic acid or water-soluble salt corresponds to the range of about 8–2000 μg of para-amine salicylic acid per ml of stabilized solution.

8. The stabilized solution of peroxidase according to claim 6, wherein said aqueous medium is an aqueous Tris buffer solution which dissolves said peroxidase and forms a water-soluble amine salt of said para-amine-salicylic acid.

9. The stabilizing solution of peroxidase according to claim 6, which further comprises 2% serum.

10. The stabilized solution of peroxidase according to claim 6, which further comprises at least 0.01% by weight of CaCl$_2$ and at least 0.01% by weight of MgCl$_2$·.6 H$_2$O.

11. The stabilized solution of peroxidase according to claim 6 wherein said water-soluble salt is of an alkali or alkaline earth metal, ammonia or an amine.

12. The stabilized solution of claim 6 wherein said peroxidase is coupled to immunological carrier particles suspended in said aqueous solution.

13. The stabilized solution of peroxidase according to claim 6, wherein the concentration of said peroxidase is not greater than 50 μg/ml of the total solution, whereby the solution is ready for use without dilution.

* * * * *